(12) United States Patent
Hernandez et al.

(10) Patent No.: US 11,116,779 B2
(45) Date of Patent: Sep. 14, 2021

(54) METHODS FOR MODULATING CORTICOSTERONE LEVELS IN PSYCHOLOGICALLY STRESSED INDIVIDUALS

(71) Applicant: ABBOTT LABORATORIES, Abbott Park, IL (US)

(72) Inventors: Enrique Vazquez Hernandez, Ogijares (ES); Ricardo Rueda Cabrera, Granada (ES); Rachael Buck, Gahanna, OH (US); Maria Ramirez Gonzalez, Granada (ES)

(73) Assignee: ABBOTT LABORATORIES, Abbott Park, IL (US)

( * ) Notice: Subject to any disclaimer, the term of this patent is extended or adjusted under 35 U.S.C. 154(b) by 0 days.

(21) Appl. No.: 16/557,461

(22) Filed: Aug. 30, 2019

(65) Prior Publication Data

US 2019/0381077 A1    Dec. 19, 2019

Related U.S. Application Data

(62) Division of application No. 14/428,260, filed as application No. PCT/US2013/059436 on Sep. 12, 2013, now Pat. No. 10,398,716.

(30) Foreign Application Priority Data

Sep. 14, 2012    (EP) ..................... 12382354

(51) Int. Cl.
| *A61K 31/702* | (2006.01) |
| *A61K 9/00* | (2006.01) |
| *A23L 33/21* | (2016.01) |
| *A23L 33/00* | (2016.01) |

(52) U.S. Cl.
CPC ............ *A61K 31/702* (2013.01); *A23L 33/21* (2016.08); *A23L 33/40* (2016.08); *A61K 9/0095* (2013.01); *A23V 2002/00* (2013.01)

(58) Field of Classification Search
None
See application file for complete search history.

(56) References Cited

U.S. PATENT DOCUMENTS

| 5,891,689 A | 4/1999 | Takle et al. |
| 2008/0021096 A1 | 1/2008 | Maher |
| 2011/0104716 A1 | 5/2011 | Mohejeri |
| 2011/0206649 A1 | 8/2011 | Bergonzelli et al. |
| 2012/0172307 A1 | 7/2012 | Davis et al. |
| 2012/0172319 A1 | 7/2012 | Chow et al. |
| 2012/0172327 A1 * | 7/2012 | Buck ...................... A23L 33/12 514/54 |
| 2015/0231159 A1 | 8/2015 | Hernandez |
| 2015/0238508 A1 | 8/2015 | Hernandez |

FOREIGN PATENT DOCUMENTS

| CA | 2822219 | 7/2012 | |
| CA | 2822222 | 7/2012 | |
| CA | 2822500 | 7/2012 | |
| CA | 2822660 | 7/2012 | |
| CA | 2822664 | 7/2012 | |
| CN | 102459295 | 5/2012 | |
| WO | 1996/09299 | 3/1996 | |
| WO | 2010/115934 | 10/2010 | |
| WO | 2011/005681 | 1/2011 | |
| WO | 2012/092155 | 7/2012 | |
| WO | 2012/092156 | 7/2012 | |
| WO | 2012/092160 | 7/2012 | |
| WO | WO-2012092160 A2 * | 7/2012 | .............. A61P 25/00 |
| WO | 2013/057049 A | 4/2013 | |

OTHER PUBLICATIONS

International Search Report and Written Opinion for PCT/US2013/059436 dated Nov. 11, 2013.
International Preliminary Report on Patentability for PCT/US2013/059436 dated Mar. 17, 2015.
International Search Report and Written Opinion for PCT/US2013/059488 dated Oct. 25, 2013.
International Preliminary Report on Patentability for PCT/US2013/059488 dated Mar. 17, 2015.
Office Action in U.S. Appl. No. 14/428,260 dated Nov. 3, 2016.
Office Action in U.S. Appl. No. 14/428,260 dated Jun. 16, 2017.
Office Action in U.S. Appl. No. 14/428,247 dated Jan. 4, 2016.
Office Action in U.S. Appl. No. 14/428,247 dated Oct. 7, 2016.
Office Action in U.S. Appl. No. 14/428,247 dated Mar. 9, 2018.
Office Action in U.S. Appl. No. 14/428,247 dated Nov. 29, 2018.
Office Action in CA Application No. 2,884,487 dated Jun. 3, 2016.
First Office Action for CN Application No. 201380059274.1 dated Jan. 28, 2016.
Second Office Action for CN Application No. 201380059274.1 dated Nov. 17, 2016.
Communication in EP Application No. 12382354.4 dated Apr. 21, 2015.
Exam Report from Malaysian Application No. PI 2015000645 dated Nov. 30, 2017.
Invitation to Respond to Written Opinion in SG Application No. 11201501976S dated Jan. 10, 2017.
Kunz, et al., "Lactose-Derived Oligosaccharides in the Milk of Elephants: Comparison with Human Milk," British Journal of Nutrition, vol. 82(5), pp. 391-399 (Nov. 1, 1999).

(Continued)

*Primary Examiner* — Traviss C McIntosh, III

(74) *Attorney, Agent, or Firm* — Calfee, Halter & Griswold LLP

(57) ABSTRACT

Disclosed are methods of modulating and/or decreasing serum corticosterone levels in an individual affected by stress. Further disclosed are methods of modulating the hypothalamic pituitary adrenal response in an individual. The methods include administration of 2-fucosyl-lactose to an individual.

16 Claims, 1 Drawing Sheet

(56) References Cited

OTHER PUBLICATIONS

Kunz, et al., "Oligosaccharides in Human Milk: Structural, Functional, and Metabolic Aspects," Annual Review of Nutrition, vol. 20 (Jan. 2000), pp. 699-722.
Matthies et al., "Fucose and fucosyllactose enhance in-vitro hippocampal long-term potentiation," Brain Research, vol. 725, No. 2, pp. 276-280, Jul. 1, 1996.
Wang, Bing et al., "Dietary sialic acid supplementation improves learning and memory in piglets," Am. J. Clin. Nutr., vol. 85(2), pp. 561-569 (Jan. 2007).
Office Action in U.S. Appl. No. 14/428,260 dated Aug. 27, 2018.
English translation of First Office Action for CN Application No. 201380059247.4 dated Jan. 15, 2016.
Communication in EP Application No. 12382356.9 dated Feb. 19, 2019.
Exam Report from Malaysian Application No. PI 2015000615 dated Jan. 31, 2020.
Exam Report from Malaysian Application No. PI 2015000645 dated May 15, 2019.
Notice of Allowance in U.S. Appl. No. 14/428,260 dated Apr. 8, 2019.
Notice of Allowance in U.S. Appl. No. 14/428,247 dated Apr. 25, 2019.
Search Report from European Application No. 20161856.8 dated Aug. 6, 2020.
Notice of Opposition from European Application No. 12382356.9 dated Dec. 10, 2020.
Blair C., "Stress and the Development of Self-Regulation in context," Child Dev Perspect, 2010; 4(3) pp. 181-188.
Bliss et al., "A Synaptic Model of Memory: Long-Term Potentiation in the Hippocampus," Nature, vol. 361, Jan. 7, 1993, pp. 31-39.
Bode et al., "Human Milk Oligosaccharides: Every Baby Needs a Sugar Mama," Glycobiology vol. 22, No. 9, 2012, pp. 1147-1162.
Disterhoft et al. "Alterations in intrinsic neuronal excitability during normal aging" Aging Cell (2007) 6 pp. 327-336.
Fenoglio et al., "Hippocampal neuroplasticity induced by early-life stress: Functional and molecular aspects" Neuroendocrinol, Jul. 2006 27(2), pp. 180-192.
Fumiyuki C et al. Preterm stress behaviors, autonomic indices and maternal perceptions of infant colic. Adv Neonatal Care, (2018) 18(1) pp. 49-57.
Kaczorowski C et al. "Memory deficits are associated with impaired ability to modulate neuronal excitability in middle-aged mice," Learning and Memory, 2009, 16: 362-366.
Krug et al., "Fucose and Fucose-Containing Sugar Epitopes Enhance Hippocampal Long-Term Potentiation in the Ferely Moving Rat," Brain Research 643, 1994, pp. 130-135.
Matthies, Jr. et al. "Enhancement of hippocampal long-term potentiation in vitro by fucosyl-carbohydrates," Section 32: Cell Adhesion in Neural Plasticity Induced by Experience. Neurochemistrv, 1997, pp. 905-908.
McClelland et al., "Emerging Roles of Epigenetic Mechanisms in the Enduring Effects of Early-Life Stress and Experience on Learning and Memory," Neurobiology of Leaning and Memory 96, 2011, p. 79-88.
McCutcheon et al., "Technical Spotlight Age Matters," European Journal of Neuroscience, vol. 29, 2009, pp. 997-1014.
Oh et al. "Learning and aging related changes in intrinsic neuronal excitability" Frontiers in Aging Neuroscience Feb. 3, 2010, vol. 2(2) pp. 1-10.
Pechtel P et al., "Effects of early life stress on cognitive and affective function: an integrated review of human literature," Psychopharmacology (Berl.) (Mar. 2011; 214(1) pp. 55-70.
Picklesimer, "Metabolic Engineer Synthesizes Key Breast Milk Ingredient, Makes Research Possible," College of Agricultural, Consumer and Environmental Sciences—Aces News, Sep. 10, 2012, 4 pages.
Wetzel et al., "Effect of L-fucose on brain protein metabolism and retention of a learned behaviour in rats," Pharmacology Biochemistry & Behavior, vol. 13, Dec. 1980, pp. 765-771.
Murrey et al., The Chemical Neurobiology of Carbohydrates, Chem. Rev. 2008, 108, pp. 1708-1741.
Reckitt Benckiser Health Limited Notice of Opposition from European Application No. 12382356.9 dated Dec. 16, 2020.
Societe des Produits Nestle S.A Notice of Opposition from European Application No. 12382356.9 dated Dec. 16, 2020.
N.V. Nutricia Notice of Opposition from European Application No. 12382356.9 dated Dec. 16, 2020.

* cited by examiner

METHODS FOR MODULATING CORTICOSTERONE LEVELS IN PSYCHOLOGICALLY STRESSED INDIVIDUALS

CROSS-REFERENCE TO RELATED APPLICATION

This application is a divisional of U.S. application Ser. No. 14/428,260, filed Mar. 13, 2015, which is the U.S. national stage entry of PCT/US2013/059436 with an international filing date of Sep. 12, 2013, which claims priority to and any other benefit of EP application 12382354.4, filed Sep. 14, 2012, entitled "METHODS FOR MODULATING CORTICOSTERONE LEVELS IN PSYCHOLOGICALLY STRESSED INDIVIDUALS," the entire disclosures of which are incorporated by reference herein.

FIELD OF THE DISCLOSURE

The present disclosure relates to human milk oligosaccharides for reducing exacerbated stress response in individuals, particularly individuals who were affected by acute psychological stress early in life. More particularly, the present disclosure relates to methods of using fucosylated human milk oligosaccharides, and in particular, 2-fucosyl-lactose (2FL), to modulate and/or decrease exacerbated serum corticosterone levels and/or modulate the hypothalamic pituitary adrenal response in an individual affected by stress.

BACKGROUND OF THE DISCLOSURE

The body's ability to keep a steady homeostatic state is crucial to the health and life of an individual. This involves providing an adequate response to a variety of challenges both physical and mental, such as microbial invasion and emotional distress. Interplay between the neuroendocrine and immune systems is essential in either case. The hypothalamic-pituitary-adrenal (HPA) axis is responsible for initiation of glucocorticoid stress responses in all vertebrate animals.

Further, there are various mechanisms that modulate HPA activity, particularly by stimulating and inhibiting stress responses, as a hyperactivated HPA response leads to an imbalanced physiological system in the individual, thereby negatively affecting the immune and gastrointestinal systems, metabolic rates, as well as cognitive function. An imbalanced physiological system can further induce mood disorders and depression.

A classical view of the neuroendocrine-immune network includes bidirectional interactions in which pro-inflammatory cytokines influence HPA axis-derived hormones (e.g., corticosterone, cortisol, aldosterone) that subsequently affect those cytokines in a feedback mechanism. These cytokines and other hormones are functionally expressed in Fintermingled network of molecules that are redundantly expressed, the elucidation of the unique roles of HPA axis-related molecules is one of particular interest.

Early life stress has been reported to induce long lasting, and in some cases, permanent changes in the central nervous system, inducing hyperactivated HPA responses. This leads to exacerbated stress responses in further stressful situations, as well as induces alterations in behavior, such as increasing anxiety-related responses, aggressiveness, future maternal care abilities, and the like. Early life stress also affects other central nervous system parameters such as the number of neurons in the hippocampus, myelination processes and neuroendocrine responses, as well as other bodily functions, including lipid metabolism and inflammatory responses.

It would therefore be desirable to provide compositions that provide individual components that will reduce hyperactivated HPA responses in individuals. It would further be beneficial to provide nutritional compositions that modulate and/or decrease exacerbated production of serum corticosterone and/or modulate HPA responses in individuals affected by stress.

SUMMARY OF THE DISCLOSURE

The present disclosure is directed to methods of reducing stress response in animals, including in individuals, including infants, pediatrics, adults, and older adults, using human milk oligosaccharides, and in particular, 2-fucosyl-lactose. 2-fucosyl-lactose modulates the hypothalamic pituitary adrenal response, thereby decreasing serum corticosterone levels in individuals affected by acute psychological stress.

In one embodiment, the present disclosure is directed to a method of modulating serum corticosterone levels in an animal. The method comprises administering to the animal a composition comprising 2-fucosyl-lactose.

In another embodiment, the present disclosure is directed to a method of decreasing serum corticosterone levels in an individual affected by stress. The method comprises administering to the individual a nutritional composition comprising 2-fucosyl-lactose.

In another embodiment the present disclosure is directed to a method of modulating hypothalamic pituitary adrenal response in an individual. The method comprises administering to the individual a composition comprising 2-fucosyl-lactose.

It has been unexpectedly discovered that human milk oligosaccharides, and particularly, 2-fucosyl-lactose, can reduce exacerbated stress response in an individual by mediating hyperactive hypothalamic pituitary adrenal (HPA) responses and decreasing serum corticosterone levels in individuals affected by stress, particularly acute psychological stress. As overproduction of corticosterone is closely related to central nervous system function (e.g., cognitive skills, mood disorders, depression), administration of 2-fucosyl-lactose may further promote central nervous system function, especially in stressful situations that may produce mood disorders or depression. These benefits are advantageously achieved without the complications seen with previously used oral synthetic pharmacological approaches.

DETAILED DESCRIPTION OF THE DISCLOSURE

Figure 1:
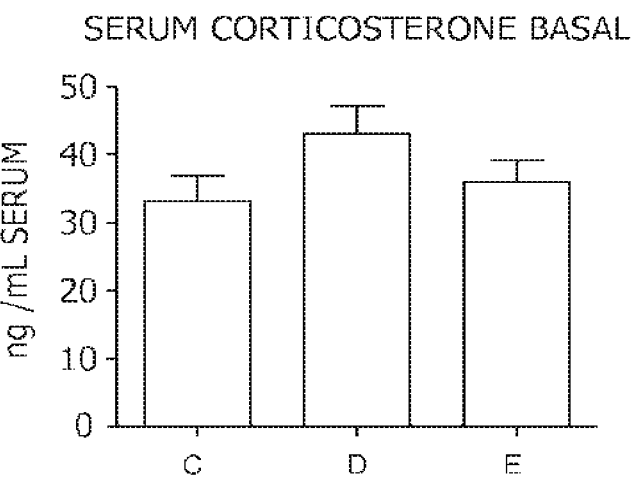
FIG. 1 is a graph depicting basal serum corticosterone levels in mice as analyzed in Example 1.

The present disclosure is directed to methods for modulating and/or decreasing serum corticosterone levels and/or modulating the hypothalamic pituitary adrenal response in an individual, thereby maintaining a balanced physiological state. The present methods include administering 2-fucosyl-lactose to an individual affected by stress, particularly stress early in life, to modulate and/or decrease serum corticosterone levels in response to stress in an individual, and further to prevent/control/reduce and/or treat hyperactivation of the HPA, and to prevent/control/reduce and/or treat malfunctions in the neuroendocrine-immune network. The methods may be useful in maintaining a healthy central nervous system, as well as have implications in the treatment of inflammation and cognitive disorders.

These and other features of the compositions and methods, as well as some of the many optional variations and additions, are described in detail hereafter.

The term "animal" as used herein refers to mammals in general, including humans.

The terms "acute psychological stress" and "acute stress" as used herein, unless otherwise specified, are used interchangeably to refer to a psychological condition (e.g., feeling of strain, pressure, anxiety, being overwhelmed, irritability, nervousness, insecurity, depression, panic, exhaustion) arising in response to a terrifying or traumatic event. A "terrifying event" or "traumatic event" is an experience that causes the individual to experience disturbing or unexpected fear, stress or pain.

The terms "early stress" or "stress early in life" as used herein, unless otherwise specified, are used interchangeably to refer to the experience of stress early in an individual's life; that is, during the period ranging from birth to early adolescence. "Early adolescence" refers to the period of from 10 years to 14 years of life.

The terms "retort packaging" and "retort sterilizing" are used interchangeably herein, and unless otherwise specified, refer to the common practice of filling a container, most typically a metal can or other similar package, with a nutritional liquid and then subjecting the liquid-filled package to the necessary heat sterilization step, to form a sterilized, retort packaged, nutritional liquid product.

The term "aseptic packaging" as used herein, unless otherwise specified, refers to the manufacture of a packaged product without reliance upon the above-described retort packaging step, wherein the nutritional liquid and package are sterilized separately prior to filling, and then are combined under sterilized or aseptic processing conditions to form a sterilized, aseptically packaged, nutritional liquid product.

The terms "fat" and "oil" as used herein, unless otherwise specified, are used interchangeably to refer to lipid materials derived or processed from plants or animals. These terms also include synthetic lipid materials so long as such synthetic materials are suitable for oral administration to humans.

The term "human milk oligosaccharide" or "HMO", as used herein, unless otherwise specified, refers generally to a number of complex carbohydrates found in human breast milk that can be in acidic or neutral form, and to precursors thereof. Exemplary non-limiting human milk oligosaccharides include 2-fucosyl-lactose, 3-fucosyl-lactose, 3-sialyl-lactose, 6-sialyl-lactose, and lacto-N-neo-tetraose. Exemplary human milk oligosaccharide precursors include sialic acid and/or fucose.

The term "shelf stable" as used herein, unless otherwise specified, refers to a nutritional product that remains commercially stable after being packaged and then stored at 18-24° C. for at least 3 months, including from about 6 months to about 24 months, and also including from about 12 months to about 18 months.

The terms "nutritional formulation" or "nutritional composition" as used herein, are used interchangeably and, unless otherwise specified, refer to synthetic formulas including nutritional liquids, nutritional powders, nutritional solids, nutritional semi-solids, nutritional semi-liquids, nutritional supplements, and any other nutritional food product as known in the art. The nutritional powders may be reconstituted to form a nutritional liquid, all of which comprise one or more of fat, protein and carbohydrate and are suitable for oral consumption by a human.

The term "nutritional liquid" as used herein, unless otherwise specified, refers to nutritional products in ready-to-drink liquid form, concentrated form, and nutritional liquids made by reconstituting the nutritional powders described herein prior to use.

The term "nutritional powder" as used herein, unless otherwise specified, refers to nutritional products in flowable or scoopable form that can be reconstituted with water or another aqueous liquid prior to consumption and includes both spray dried and drymixed/dryblended powders.

The term "nutritional semi-solid," as used herein, unless otherwise specified, refers to nutritional products that are intermediate in properties, such as rigidity, between solids and liquids. Some semi-solids examples include puddings, gelatins, and doughs.

The term "nutritional semi-liquid," as used herein, unless otherwise specified, refers to nutritional products that are intermediate in properties, such as flow properties, between liquids and solids. Some semi-liquids examples include thick shakes and liquid gels.

The terms "susceptible" and "at risk" as used herein, unless otherwise specified, mean having little resistance to a certain condition or disease, including being genetically predisposed, having a family history of, and/or having symptoms of the condition or disease.

The terms "modulating" or "modulation" or "modulate" as used herein, unless otherwise specified, refer to the targeted movement of a selected characteristic.

All percentages, parts and ratios as used herein, are by weight of the total composition, unless otherwise specified. All such weights, as they pertain to listed ingredients, are based on the active level and, therefore, do not include solvents or by-products that may be included in commercially available materials, unless otherwise specified.

Numerical ranges as used herein are intended to include every number and subset of numbers within that range, whether specifically disclosed or not. Further, these numerical ranges should be construed as providing support for a claim directed to any number or subset of numbers in that range. For example, a disclosure of from 1 to 10 should be construed as supporting a range of from 2 to 8, from 3 to 7, from 5 to 6, from 1 to 9, from 3.6 to 4.6, from 3.5 to 9.9, and so forth.

All references to singular characteristics or limitations of the present disclosure shall include the corresponding plural characteristic or limitation, and vice versa, unless otherwise specified or clearly implied to the contrary by the context in which the reference is made.

All combinations of method or process steps as used herein can be performed in any order, unless otherwise specified or clearly implied to the contrary by the context in which the referenced combination is made.

The various embodiments of the compositions for use in the methods of the present disclosure may also be substantially free of any optional or selected ingredient or feature described herein, provided that the nutritional composition still contains all of the required ingredients or features as described herein. In this context, and unless otherwise specified, the term "substantially free" means that the selected nutritional composition contains less than a functional amount of the optional ingredient, typically less than 1%, including less than 0.5%, including less than 0.1%, and also including zero percent, by weight of such optional or selected ingredient.

The compositions and methods may comprise, consist of, or consist essentially of the essential elements of the compositions and methods as described herein, as well as any additional or optional element described herein or otherwise useful in nutritional product applications.

Product Form

The compositions used in the methods of the present disclosure include a fucosylated human milk oligosaccharide, particularly 2-fucosyl-lactose (2FL), and may be formulated and administered in any known or otherwise suitable oral product form. Any solid, liquid, semi-solid, semi-liquid, or powder product form, including combinations or variations thereof, are suitable for use herein, provided that such forms allow for safe and effective oral delivery to the individual of the ingredients as also defined herein.

The compositions used in the methods of the present disclosure are desirably formulated as dietary product forms, which are defined herein as those embodiments comprising the ingredients of the present disclosure in a product form that then contains at least one of fat, protein, and carbohydrate, and preferably also contains vitamins, minerals, or combinations thereof.

The nutritional compositions may be formulated with sufficient kinds and amounts of nutrients to provide a sole, primary, or supplemental source of nutrition, or to provide a specialized nutritional product for use in individuals afflicted with specific conditions or with a targeted nutritional benefit as described below.

Some exemplary, non-limiting, examples of specific products that may be suitable for use in accordance with the present disclosure include preterm infant formulas, term infant formulas, human milk fortifiers, pediatric formulas, adult nutritional formulas, older adult nutritional formulas, medical formulas, geriatric nutritional formulas, diabetic nutritional formulas, and the like.

Nutritional Liquids

Nutritional liquids include both concentrated and ready-to-feed nutritional liquids. These nutritional liquids are most typically formulated as suspensions or emulsions, although other liquid forms are within the scope of the present disclosure.

Nutritional emulsions suitable for use may be aqueous emulsions comprising proteins, fats, and carbohydrates. These emulsions are generally flowable or drinkable liquids at from about 1° C. to about 25° C. and are typically in the form of oil-in-water, water-in-oil, or complex aqueous emulsions, although such emulsions are most typically in the form of oil-in-water emulsions having a continuous aqueous phase and a discontinuous oil phase.

The nutritional emulsions may be and typically are shelf stable. The nutritional emulsions typically contain up to 95% by weight of water, including from about 50% to 95%, also including from about 60% to about 90%, and also including from about 70% to about 85%, of water by weight of the nutritional emulsions. The nutritional emulsions may have a variety of product densities, but most typically have a density greater than 1.03 g/mL, including greater than 1.04 g/mL, including greater than 1.055 g/mL, including from about 1.06 g/mL to about 1.12 g/mL, and also including from about 1.085 g/mL to about 1.10 g/mL.

The nutritional emulsions may have a caloric density tailored to the nutritional needs of the ultimate user, although in most instances the emulsions comprise generally at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the emulsion may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

The nutritional emulsion may have a pH ranging from about 3.5 to about 8, but are most advantageously in a range of from about 4.5 to about 7.5, including from about 5.5 to about 7.3, including from about 6.2 to about 7.2.

Although the serving size for the nutritional emulsion can vary depending upon a number of variables, a typical serving size is generally at least 1 mL, or even at least 2 mL, or even at least 5 mL, or even at least 10 mL, or even at least 25 mL, including ranges from 1 mL to about 300 mL, including from about 4 mL to about 250 mL, and including from about 10 mL to about 240 mL.

Nutritional Solids

The nutritional solids may be in any solid form but are typically in the form of flowable or substantially flowable particulate compositions, or at least particulate compositions. Particularly suitable nutritional solid product forms include spray dried, agglomerated and/or dryblended powder compositions. The compositions can easily be scooped and measured with a spoon or similar other device, and can easily be reconstituted by the intended user with a suitable aqueous liquid, typically water, to form a nutritional composition for immediate oral or enteral use. In this context, "immediate" use generally means within about 48 hours, most typically within about 24 hours, preferably right after reconstitution.

The nutritional powders may be reconstituted with water prior to use to a caloric density tailored to the nutritional needs of the ultimate user, although in most instances the powders are reconstituted with water to form compositions comprising at least 19 kcal/fl oz (660 kcal/liter), more typically from about 20 kcal/fl oz (675-680 kcal/liter) to about 25 kcal/fl oz (820 kcal/liter), even more typically from about 20 kcal/fl oz (675-680 kcal/liter) to about 24 kcal/fl oz (800-810 kcal/liter). Generally, the 22-24 kcal/fl oz formulas are more commonly used in preterm or low birth weight infants, and the 20-21 kcal/fl oz (675-680 to 700 kcal/liter) formulas are more often used in term infants. In some embodiments, the reconstituted powder may have a caloric density of from about 50-100 kcal/liter to about 660 kcal/liter, including from about 150 kcal/liter to about 500 kcal/liter. In some specific embodiments, the emulsion may have a caloric density of 25, or 50, or 75, or 100 kcal/liter.

Methods of Modulating Hypothalamic Pituitary Adrenal (HPA) Response and Serum Corticosterone Levels The methods of the present disclosure use fucosylated human milk oligosaccharides-containing nutritional compositions, and in particular, 2-fucosyl-lactose (2FL)-containing nutritional compositions, to modulate hypothalamic pituitary adrenal (HPA) response in an individual. As noted, HPA response initiates the glucocorticoid stress response in vertebrate animals. During an acute psychological stressful event, stress hormones (e.g., corticosterone) are released from the HPA axis, affecting the release and expression of cytokines in the central nervous system as well as in immune cells. Hyperactivation of HPA leads to an over-release of hormones, which can be damaging to various physiological systems in the body of the individual, negatively affecting, for example, the immune and gastrointestinal systems, metabolic rate, and cognitive function. Particularly, hyperactivation of HPA may induce alterations in behavior, increasing anxiety, periods of depression, and aggressiveness, as well as negatively affect lipid metabolism, inflammatory responses, and gastrointestinal health. The methods of the present disclosure that modulate/prevent/control/reduce and/or treat HPA responses are beneficial for a wide range of individuals, including preterm infants, infants, pediatric individuals, teens, adults, and older adults (adults at least 50 or more years of age).

The methods further may be useful in preventing/controlling/reducing and/or treating malfunctions in the neuroendocrine-immune network that can result from a hyperactivated HPA response. Thereby, these methods maintain a healthy central nervous system, immunity system and healthy gastrointestinal system. The administration of 2FL may further have implications in the treatment of inflammation and cognitive disorders.

Additionally, the methods of the present disclosure include modulating and/or decreasing the production of serum corticosterone in an individual, particularly an individual affected by stress. Overproduction of corticosterone, typically a consequence of hyperactivated HPA response, leads to exacerbated stress responses in further stressful situations, as well as induces alterations in behavior, such as increasing anxiety-related responses, aggressiveness, future maternal care abilities, and the like. By modulating and/or reducing the production of serum corticosterone in an individual, including preterm infants, infants, pediatric individuals, teens, adults, and older adults, these behavioral defects can be prevented/controlled/reduced and/or treated.

Further, as overproduction of corticosterone is closely related to central nervous system function (e.g., cognitive skills, mood disorders, depression), the methods of the present disclosure may further promote central nervous system function, especially in stressful situations, thereby preventing/controlling/reducing and/or treating occurrences of mood disorders or depression.

2-fucosyl-lactose (2FL) may be administered to a subset of individuals in need of modulation or reduction of serum corticosterone levels and/or modulation of the HPA response. Some individuals that are in specific need of modulated or decreased serum corticosterone levels or modulated HPA responses may include infants, pediatrics, teens, or adults who experience acute psychological stress or stressful events (infants, pediatrics, teens, or adults susceptible to or at elevated risk of experiencing acute psychological stress or stressful events), infants, pediatrics, teens, or adults who experienced acute psychological stress early in life, non-breastfed infants, chronically depressed infants, pediatrics, teens, or adults (infants, pediatrics, teens, or adults susceptible to or at elevated risk of chronic depression), infants, pediatrics, teens, or adults affected by post-traumatic stress syndrome (infants, pediatrics, teens, or adults susceptible to or at elevated risk of post-traumatic stress syndrome) and the like. Preterm infants, infants, pediatrics, teens, adults, and older adults may be susceptible to or at elevated risk for experiencing acute psychological stress or stressful events due to family history, age, environment, and/or lifestyle. Based on the foregoing, because some of the method embodiments of the present disclosure are directed to specific subsets or subclasses of identified individuals (that is, the subset or subclass of individuals "in need" of assistance in addressing one or more specific conditions noted herein), not all individuals will fall within the subset or subclass of individuals as described herein for certain diseases or conditions.

The individual desirably consumes at least one serving of the nutritional composition daily, and in some embodiments, may consume two, three, or even more servings per day. Each serving is desirably administered as a single, undivided dose, although the serving may also be divided into two or more partial or divided servings to be taken at two or more times during the day. The methods of the present disclosure include continuous day after day administration, as well as periodic or limited administration, although continuous day after day administration is generally desirable. The methods of the present disclosure are preferably applied on a daily basis, wherein the daily administration is maintained continuously for at least 3 days, including at least 5 days, including at least 1 month, including at least 4 weeks, including at least 8 weeks, including at least 2 months, including at least 6 months, desirably for at least 18-24 months, desirably as a long term, continuous, daily, dietary supplement.

2-Fucosyl-lactose (2FL)

The methods of the present disclosure for modulating and/or decreasing serum corticosterone levels and/or modulating HPA responses utilize compositions that include 2-fucosyl-lactose (2FL). The 2FL used in the composition may be isolated or enriched from milk(s) secreted by mammals including, but not limited to: human, bovine, ovine, porcine, or caprine species. 2FL may also be produced via microbial fermentation, enzymatic processes, chemical synthesis, or combinations thereof.

2FL is present in the compositions in an amount (mg of 2FL per mL of composition) of at least 0.001 mg/mL, including at least 0.01 mg/mL, including from 0.001 mg/mL to about 20 mg/mL, including from about 0.01 mg/mL to about 20 mg/mL, including from 0.001 mg/mL to about 10 mg/mL, including from about 0.01 mg/mL to about 10 mg/mL, including from 0.001 mg/mL to about 5 mg/mL, including from about 0.01 mg/mL to about 5 mg/mL, including from 0.001 mg/mL to about 1 mg/mL, including from 0.001 mg/mL to about 0.23 mg/mL, including from about 0.01 mg/mL to about 0.23 mg/mL of 2FL in the composition. Typically, the amount of 2FL present in the composition will depend on the amounts of other components in the compositions, including the amounts any optional other human milk oligosaccharides as described below.

In one specific embodiment when the composition is a nutritional powder, the concentration of 2FL in the nutritional powder is from about 0.0005% to about 5%, including from about 0.01% to about 1% (by weight of the nutritional powder).

In another specific embodiment, when the product is a ready-to-feed nutritional liquid, the concentration of 2FL in the ready-to-feed nutritional liquid is from about 0.0001% to about 0.50%, including from about 0.001% to about 0.15%, including from about 0.01% to about 0.10%, and further including from about 0.01% to about 0.03% (by weight of the ready-to-feed nutritional liquid).

In another specific embodiment when the product is a concentrated nutritional liquid, the concentration of 2FL in the concentrated nutritional liquid is from about 0.0002% to about 0.60%, including from about 0.002% to about 0.30%, including from about 0.02% to about 0.20%, and further including from about 0.02% to about 0.06% (by weight of the concentrated nutritional liquid).

Optional Additional Sialylated or Fucosylated Human Milk Oligosaccharides

In addition to the 2FL described above, the compositions may optionally include additional sialylated or fucosylated human milk oligosaccharides. The additional human milk oligosaccharide(s) used in the composition may be isolated or enriched from milk(s) secreted by mammals including, but not limited to: human, bovine, ovine, porcine, or caprine species. The human milk oligosaccharides may also be produced via microbial fermentation, enzymatic processes, chemical synthesis, or combinations thereof.

Suitable sialylated human milk oligosaccharides for optional use in the compositions include at least one sialic acid residue in the oligosaccharide backbone. The sialylated human milk oligosaccharide may include two or more sialic acid residues also. Specific non-limiting examples of sialylated human milk oligosaccharides for use in the present disclosure include sialyl oligosaccharides, sialic acid (i.e., free sialic acid, lipid-bound sialic acid, protein-bound sialic acid), lactosialotetraose, 3'-Sialyl-3-fucosyllactose, Di sialo-monofucosyllacto-N-neohexaose, Monofucosylmonosialyl-lacto-N-octaose (sialyl Lea), Sialyllacto-N-fucohexaose II, Disialyllacto-N-fucopentaose II, Monofucosyldisialyllacto-N-tetraose), sialyl fucosyl oligosaccharides, 2'-Sialyllactose, 2-Sialyllactosamine, 3'-Sialyllactose, 3'-Sialyllactosamine, 6'-Sialyllactose, 6'-Sialyllactosamine, Sialyllacto-N-neotetraose c, Monosialyllacto-N-hexaose, Disialyllacto-N-hexaose I, Monosialyllacto-N-neohexaose I, Monosialyl-lacto-N-neohexaose II, Disialyllacto-N-neohexaose, Disialyllacto-N-tetraose, Disialyllacto-N-hexaose II, Sialyl-lacto-N-tetraose a, Disialyllacto-N-hexaose I, Sialyllacto-N-tetraose b, sialyl-lacto-N-tetraose a, sialyl-lacto-N-tetraose b, sialyl-lacto-N-tetraose c, sialyl-fucosyl-lacto-N-tetraose I, sialyl-fucosyl-lacto-N-tetraose II, disialyl-lacto-N-tetraose and combinations thereof. Particularly desirable sialylated human milk oligosaccharides include 3'Sialyllactose, 6'Sialyllactose, and combinations thereof.

Specific non-limiting examples of additional optional fucosylated human milk oligosaccharides for use in the present disclosure include fucosyl oligosaccharides, Lacto-N-fucopentaose I, Lacto-N-fucopentaose II, 3'-Fucosyllactose, Lacto-N-fucopentaose III, Lacto-N-difucohexaose I, Lactodifucotetraose, monofucosyllacto-N-hexaose II, isomeric fucosylated lacto-N-hexaose (1), isomeric fucosylated lacto-N-hexaose (3), isomeric fucosylated lacto-N-hexaose (2), difucosyl-para-lacto-N-neohexaose, difucosyl-para-lacto-N-hexaose, difucosyllacto-N-hexaosemonofucosyl-lacto-neoocataose, monofucosyllacto-N-ocataose, difucosyllacto-N-octaose I, difucosyllacto-N-octaose II, difucosyllacto-N-neoocataose II, difucosyllacto-N-neoocataose I, lacto-N-fucopentaose V, lacto-N-decaose, trifucosyl-lacto-N-neooctaose, trifucosyllacto-N-octaose, trifucosyl-iso-lacto-N-octaose, lacto-N-difuco-hexaose II, and combinations thereof.

Other suitable examples of human milk oligosaccharides that may be included in the compositions for use in the methods of the present disclosure include lacto-N-hexaose, para-lacto-N-hexaose, lacto-N-neohexaose, para-lacto-N-neohexaose, lacto-N-neoocataose, para-lacto-N-octanose, iso-lacto-N-octaose, lacto-N-octaose, and combinations thereof.

The sialylated and fucosylated human milk oligosaccharides (inclusive of 2FL) may be present in the compositions in a total amount of human milk oligosaccharide in the composition (mg of human milk oligosaccharide per mL of composition) of at least 0.001 mg/mL, including at least 0.01 mg/mL, including from 0.001 mg/mL to about 20 mg/mL, including from about 0.01 mg/mL to about 20 mg/mL, including from 0.001 mg/mL to about 10 mg/mL, including from about 0.01 mg/mL to about 10 mg/mL, including from 0.001 mg/mL to about 5 mg/mL, including from about 0.01 mg/mL to about 5 mg/mL, including from 0.001 mg/mL to about 1 mg/mL, including from 0.001 mg/mL to about 0.23 mg/mL, including from about 0.01 mg/mL to about 0.23 mg/mL of total human milk oligosaccharide in the composition. Typically, the amount of specific sialylated human milk oligosaccharide and/or fucosylated human milk oligosaccharide (inclusive of 2FL) present in the composition will depend on the specific human milk oligosaccharide or human milk oligosaccharides present and the amounts of other components in the compositions, including the amounts of any optional human milk oligosaccharides.

Macronutrients

The compositions including 2FL may be formulated to include at least one of fat, protein, and carbohydrate. In many embodiments, the nutritional compositions will include 2FL with fat, protein, and carbohydrate.

Although total concentrations or amounts of the fat, protein, and carbohydrates may vary depending upon the product type (i.e., human milk fortifier, preterm infant formula, infant formula, pediatric formula, adult formula, medical formula, etc.), product form (i.e., nutritional solid, powder, ready-to-feed liquid, or concentrated liquid) and targeted dietary needs of the intended user, such concentrations or amounts most typically fall within one of the following embodied ranges, inclusive of any other essential fat, protein, and/or carbohydrate ingredients as described herein.

For infant and adult formulas, carbohydrate concentrations most typically range from about 5% to about 40%, including from about 7% to about 30%, including from about 10% to about 25%, by weight; fat concentrations most typically range from about 1% to about 30%, including from about 2% to about 15%, and also including from about 3% to about 10%, by weight; and protein concentrations most typically range from about 0.5% to about 30%, including from about 1% to about 15%, and also including from about 2% to about 10%, by weight.

The amount of fats, proteins, and/or carbohydrates in any of the liquid nutritional compositions described herein may also be characterized in addition to, or in the alternative, as a percentage of total calories in the liquid nutritional composition as set forth in the following table. These macronutrients for liquid nutritional compositions of the present disclosure are most typically formulated within any of the caloric ranges (embodiments A-F) described in the following table (each numerical value is preceded by the term "about").

| Nutrient % Total Cal. | Embodiment A | Embodiment B | Embodiment C |
| --- | --- | --- | --- |
| Carbohydrate | 0-98 | 2-96 | 10-75 |
| Protein | 0-98 | 2-96 | 5-70 |
| Fat | 0-98 | 2-96 | 20-85 |
| | Embodiment D | Embodiment E | Embodiment F |
| Carbohydrate | 30-50 | 25-50 | 25-50 |
| Protein | 15-35 | 10-30 | 5-30 |
| Fat | 35-55 | 1-20 | 2-20 |

In one specific example, liquid infant formulas (both ready-to-feed and concentrated liquids) include those embodiments in which the protein component may comprise from about 7.5% to about 25% of the caloric content of the formula; the carbohydrate component may comprise from about 35% to about 50% of the total caloric content of the infant formula; and the fat component may comprise from about 30% to about 60% of the total caloric content of the infant formula. These ranges are provided as examples only, and are not intended to be limiting. Additional suitable ranges are noted in the following table (each numerical value is preceded by the term "about").

| Nutrient % Total Cal. | Embodiment G | Embodiment H | Embodiment I |
|---|---|---|---|
| Carbohydrates: | 20-85 | 30-60 | 35-55 |
| Fat: | 5-70 | 20-60 | 25-50 |
| Protein: | 2-75 | 5-50 | 7-40 |

When the nutritional product is a powdered preterm or term infant formula, the protein component is present in an amount of from about 5% to about 35%, including from about 8% to about 12%, and including from about 10% to about 12% by weight of the preterm or term infant formula; the fat component is present in an amount of from about 10% to about 35%, including from about 25% to about 30%, and including from about 26% to about 28% by weight of the preterm or term infant formula; and the carbohydrate component is present in an amount of from about 30% to about 85%, including from about 45% to about 60%, including from about 50% to about 55% by weight of the preterm or term infant formula.

For powdered human milk fortifiers the protein component is present in an amount of from about 1% to about 55%, including from about 10% to about 50%, and including from about 10% to about 30% by weight of the human milk fortifier; the fat component is present in an amount of from about 1% to about 30%, including from about 1% to about 25%, and including from about 1% to about 20% by weight of the human milk fortifier; and the carbohydrate component is present in an amount of from about 15% to about 75%, including from about 15% to about 60%, including from about 20% to about 50% by weight of the human milk fortifier.

The total amount or concentration of fat, carbohydrate, and protein, in the powdered nutritional compositions used herein can vary considerably depending upon the selected composition and dietary or medical needs of the intended user. Additional suitable examples of macronutrient concentrations are set forth below. In this context, the total amount or concentration refers to all fat, carbohydrate, and protein sources in the powdered product. For powdered nutritional compositions, such total amounts or concentrations are most typically and preferably formulated within any of the embodied ranges described in the following table (each numerical value is preceded by the term "about").

| Nutrient % Total Cal. | Embodiment J | Embodiment K | Embodiment L |
|---|---|---|---|
| Carbohydrate | 1-85 | 30-60 | 35-55 |
| Fat | 5-70 | 20-60 | 25-50 |
| Protein | 2-75 | 5-50 | 7-40 |

Fat

The nutritional compositions used in the methods of the present disclosure may include a source or sources of fat. Suitable sources of fat for use herein include any fat or fat source that is suitable for use in an oral nutritional product and is compatible with the elements and features of such products. For example, in one specific embodiment, the fat is derived from long chain polyunsaturated fatty acids and/or short chain fatty acids.

Additional non-limiting examples of suitable fats or sources thereof for use in the nutritional products described herein include coconut oil, fractionated coconut oil, soybean oil, corn oil, olive oil, safflower oil, high oleic safflower oil, oleic acids (EMERSOL 6313 OLEIC ACID, Cognis Oleochemicals, Malaysia), MCT oil (medium chain triglycerides), sunflower oil, high oleic sunflower oil, palm and palm kernel oils, palm olein, canola oil, marine oils, fish oils, fungal oils, algae oils, cottonseed oils, and combinations thereof.

Protein

The nutritional compositions used in the methods of the present disclosure may optionally further comprise protein. Any protein source that is suitable for use in oral nutritional compositions and is compatible with the elements and features of such products is suitable for use in the nutritional compositions.

Non-limiting examples of suitable proteins or sources thereof for use in the nutritional products include hydrolyzed, partially hydrolyzed or non-hydrolyzed proteins or protein sources, which may be derived from any known or otherwise suitable source such as milk (e.g., casein, whey), animal (e.g., meat, fish), cereal (e.g., rice, corn), vegetable (e.g., soy, pea) or combinations thereof. Non-limiting examples of such proteins include milk protein isolates, milk protein concentrates as described herein, casein protein isolates, extensively hydrolyzed casein, whey protein, sodium or calcium caseinates, whole cow milk, partially or completely defatted milk, soy protein isolates, soy protein concentrates, intact pea protein concentrates, intact pea protein isolates, hydrolyzed pea protein concentrates, hydrolyzed pea protein isolates, and so forth. In one specific embodiment, the nutritional compositions include a protein source derived from milk proteins of human and/or bovine origin.

Carbohydrate

The nutritional products as used in the methods of the present disclosure may further optionally comprise any carbohydrates that are suitable for use in an oral nutritional product and are compatible with the elements and features of such products.

Non-limiting examples of suitable carbohydrates or sources thereof for use in the nutritional products described herein may include maltodextrin, hydrolyzed or modified starch or cornstarch, glucose polymers, corn syrup, corn syrup solids, rice-derived carbohydrates, pea-derived carbohydrates, potato-derived carbohydrates, tapioca, sucrose, glucose, fructose, lactose, high fructose corn syrup, honey, sugar alcohols (e.g., maltitol, erythritol, sorbitol), artificial sweeteners (e.g., sucralose, acesulfame potassium, stevia) and combinations thereof. A particularly desirable carbohydrate is a low dextrose equivalent (DE) maltodextrin.

Other Optional Ingredients

The compositions as used in the methods of the present disclosure may further comprise other optional components that may modify the physical, chemical, aesthetic or processing characteristics of the products or serve as pharmaceutical or additional nutritional components when used in the targeted population. Many such optional ingredients are known or otherwise suitable for use in medical food or other nutritional products or pharmaceutical dosage forms and may also be used in the compositions herein, provided that such optional ingredients are safe for oral administration and are compatible with the essential and other ingredients in the selected product form.

Non-limiting examples of such optional ingredients include preservatives, emulsifying agents, buffers, fructooligosaccharides, galactooligosaccharides, polydextrose, and other prebiotics, probiotics, pharmaceutical actives, anti-inflammatory agents, additional nutrients as described herein, colorants, flavors, thickening agents and stabilizers, emulsifying agents, lubricants, and so forth.

The nutritional compositions may further comprise a sweetening agent, preferably including at least one sugar alcohol such as maltitol, erythritol, sorbitol, xylitol, mannitol, isolmalt, and lactitol, and also preferably including at least one artificial or high potency sweetener such as acesulfame K, aspartame, sucralose, saccharin, stevia, and tagatose. These sweetening agents, especially as a combination of a sugar alcohol and an artificial sweetener, are especially useful in formulating liquid beverage embodiments having a desirable favor profile. These sweetener combinations are especially effective in masking undesirable flavors sometimes associated with the addition of vegetable proteins to a liquid beverage. Optional sugar alcohol concentrations in the nutritional product may range from at least 0.01%, including from about 0.1% to about 10%, and also including from about 1% to about 6%, by weight of the nutritional product. Optional artificial sweetener concentrations may range from at least 0.01%, including from about 0.05% to about 5%, also including from about 0.1% to about 1.0%, by weight of the nutritional product.

A flowing agent or anti-caking agent may be included in the nutritional compositions as described herein to retard clumping or caking of the powder over time and to make a powder embodiment flow easily from its container. Any known flowing or anti-caking agents that are known or otherwise suitable for use in a nutritional powder or product form are suitable for use herein, non-limiting examples of which include tricalcium phosphate, silicates, and combinations thereof. The concentration of the flowing agent or anti-caking agent in the nutritional composition varies depending upon the product form, the other selected ingredients, the desired flow properties, and so forth, but most typically range from about 0.1% to about 4%, including from about 0.5% to about 2%, by weight of the nutritional composition.

A stabilizer may also be included in the nutritional compositions. Any stabilizer that is known or otherwise suitable for use in a nutritional composition is also suitable for use herein, some non-limiting examples of which include gums such as xanthan gum. The stabilizer may represent from about 0.1% to about 5.0%, including from about 0.5% to about 3%, including from about 0.7% to about 1.5%, by weight of the nutritional composition.

The nutritional compositions may further comprise any of a variety of other vitamins or related nutrients, non-limiting examples of which include vitamin A, vitamin D, vitamin E, vitamin K, thiamine, riboflavin, pyridoxine, vitamin B12, carotenoids (e.g., beta-carotene, zeaxanthin, lutein, lycopene), niacin, folic acid, pantothenic acid, biotin, vitamin C, choline, inositol, salts and derivatives thereof, and combinations thereof.

The nutritional compositions may further comprise any of a variety of other additional minerals, non-limiting examples of which include calcium, phosphorus, magnesium, iron, zinc, manganese, copper, sodium, potassium, molybdenum, chromium, chloride, and combinations thereof.

Methods of Manufacture

The nutritional compositions used in the methods of the present disclosure may be prepared by any known or otherwise effective manufacturing technique for preparing the selected product solid or liquid form. Many such techniques are known for any given product form such as nutritional liquids or powders and can easily be applied by one of ordinary skill in the art to the nutritional compositions described herein.

The nutritional compositions used in the methods of the present disclosure can therefore be prepared by any of a variety of known or otherwise effective formulation or manufacturing methods. In one suitable manufacturing process, for example, at least three separate slurries are prepared, including a protein-in-fat (PIF) slurry, a carbohydrate-mineral (CHO-MIN) slurry, and a protein-in-water (PIW) slurry. The PIF slurry is formed by heating and mixing the oil (e.g., canola oil, corn oil, etc.) and then adding an emulsifier (e.g., lecithin), fat soluble vitamins, and a portion of the total protein (e.g., milk protein concentrate, etc.) with continued heat and agitation. The CHO-MIN slurry is formed by adding with heated agitation to water: minerals (e.g., potassium citrate, dipotassium phosphate, sodium citrate, etc.), trace and ultra trace minerals (TM/UTM premix), thickening or suspending agents (e.g. avicel, gellan, carrageenan). The resulting CHO-MIN slurry is held for 10 minutes with continued heat and agitation before adding additional minerals (e.g., potassium chloride, magnesium carbonate, potassium iodide, etc.), and/or carbohydrates (e.g., 2FL, fructooligosaccharide, sucrose, corn syrup, etc.). The PIW slurry is then formed by mixing with heat and agitation the remaining protein, if any.

The resulting slurries are then blended together with heated agitation and the pH adjusted to 6.6-7.0, after which the composition is subjected to high-temperature short-time (HTST) processing during which the composition is heat treated, emulsified and homogenized, and then allowed to cool. Water soluble vitamins and ascorbic acid are added, the pH is adjusted to the desired range if necessary, flavors are added, and water is added to achieve the desired total solid level. The composition is then aseptically packaged to form an aseptically packaged nutritional emulsion. This emulsion can then be further diluted, heat-treated, and packaged to form a ready-to-feed or concentrated liquid, or it can be heat-treated and subsequently processed and packaged as a reconstitutable powder, e.g., spray dried, drymixed, agglomerated.

The nutritional solid, such as a spray dried nutritional powder or drymixed nutritional powder, may be prepared by any collection of known or otherwise effective technique, suitable for making and formulating a nutritional powder.

For example, when the nutritional powder is a spray dried nutritional powder, the spray drying step may likewise include any spray drying technique that is known for or otherwise suitable for use in the production of nutritional powders. Many different spray drying methods and techniques are known for use in the nutrition field, all of which are suitable for use in the manufacture of the spray dried nutritional powders herein.

One method of preparing the spray dried nutritional powder comprises forming and homogenizing an aqueous slurry or liquid comprising predigested fat, and optionally protein, carbohydrate, and other sources of fat, and then spray drying the slurry or liquid to produce a spray dried nutritional powder. The method may further comprise the step of spray drying, drymixing, or otherwise adding additional nutritional ingredients, including any one or more of the ingredients described herein, to the spray dried nutritional powder.

Other suitable methods for making nutritional products are described, for example, in U.S. Pat. No. 6,365,218 (Borschel, et al.), U.S. Pat. No. 6,589,576 (Borschel, et al.), U.S. Pat. No. 6,306,908 (Carlson, et al.), U.S. Patent Application No. 20030118703 A1 (Nguyen, et al.), which descriptions are incorporated herein by reference to the extent that they are consistent herewith.

EXAMPLES

The following examples illustrate specific embodiments and/or features of the nutritional compositions used in the methods of the present disclosure. The examples are given solely for the purpose of illustration and are not to be construed as limitations of the present disclosure, as many variations thereof are possible without departing from the spirit and scope of the disclosure. All exemplified amounts are weight percentages based upon the total weight of the composition, unless otherwise specified.

The exemplified compositions are shelf stable nutritional compositions prepared in accordance with the manufacturing methods described herein, such that each exemplified composition, unless otherwise specified, includes an aseptically processed embodiment and a retort packaged embodiment.

Example 1

In this Example, the effects of 2-fucosyl-lactose on the production of serum corticosterone in early stressed maternally deprived mice were analyzed.

Initially, mice pups were early stressed using a model of maternal separation. Particularly, one day after delivery, C57BL/6 mice pups were sexed and grouped as sham (non-stressed Control group) or maternally separated (MS—stressed group) animals. From day 2 until day 14 after delivery, the MS pups were removed from the dam and kept isolated for a period of 4 hours per day, typically, from 10:00 AM to 2:00 PM, in a thermostatted cup. During the same time period, pups from the sham group were daily handled for a period of five minutes in order to receive the same grade of habituation to a researcher's hands as the MS pups.

Each dam had litters of 4 males and 2 females. Females were allowed to stay with the mother, while males were maternally deprived in order to avoid stressing the dam by removing all of the pups. Additionally, pups from the MS group were prematurely weaned, and thus permanently removed from the dam, at postnatal day 17, whereas sham pups were not weaned until postnatal day 21. At postnatal day 22, all pups in the MS group were pooled and four experimental groups were made before starting nutritional intervention. The five total groups are shown in the table below.

| Experimental Group | Experimental Conditions |
| --- | --- |
| Sham Control Group (Group code E) | Normal mice not MS-stressed receiving AIN-93G diet and water. |
| MS Control Group (Group code D) | MS-stressed mice receiving AIN-93G diet and water. |
| MS 2-fucosyllactose Group (Group code C) | MS-stressed mice receiving AIN93G diet supplemented with 2-fucosyllactose in an amount of about 7 mg/mouse/day and water. |

At the nutritional intervention stage, mice were fed experimental diets for a period of eight weeks. After eight weeks, blood samples were taken from facial veins of the mice in order to measure basal stress hormones (i.e., corticosterone, adrenocorticotropic hormone (ACTH), and melatonin). Stress hormones were measured using luminex technology using a multiplex commercial kit (commercially available from Millipore Corporation, Billerica, Mass.)

Seven days later, mice were submitted to an acute stress by restraint protocol. Particularly, mice were placed into a multi-drilled 50-ml centrifuge tube for 20 minutes. After this time, mice were extracted from the tube, and again, blood samples were taken in order to measure serum stress hormones immediately after the acute stressful event (i.e., restraint). Results are shown in FIGS. 1 & 2.

Figure 2:
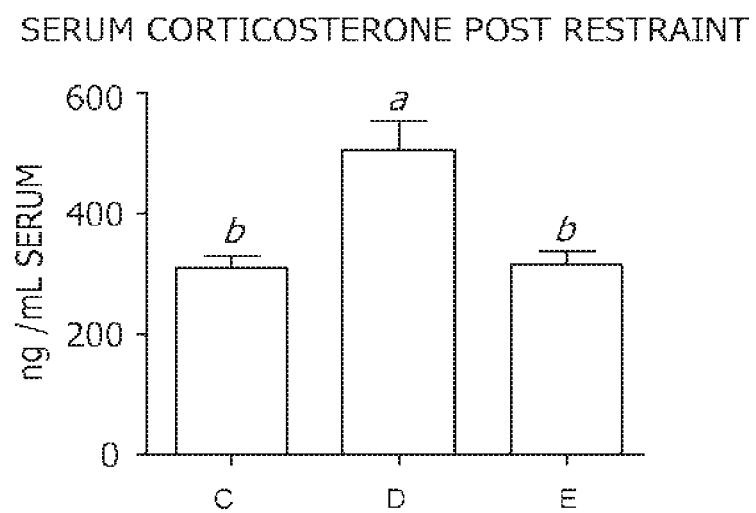
FIG. 2 is a graph depicting post restraint serum corticosterone levels in mice as analyzed in Example 1.

As shown in FIGS. 1 and 2, no effects were found on ACTH or melatonin serum levels in any of the experimental groups post-restraint. The serum corticosterone levels, however, were significantly higher in MS mice that were submitted to early infancy stress as compared to normal sham mice (see Group D). It was further found, however, that early stressed mice fed a diet supplemented with 2-fucosyl-lactose (Group C) had corticosterone levels in response to restraint that equal that of the normal sham mice and where significantly lower than the levels exhibited by MS mice on the control diet. Accordingly, it is believed that 2-fucosyl-lactose was able to counteract the exacerbated hypothalamic-pituitary-adrenal (HPA) response in response to acute stressors showed by animals submitted to an early psychological stress during infancy.

Examples 2-6

Examples 2-6 illustrate ready-to-feed nutritional emulsions used in the methods of the present disclosure, the ingredients of which are listed in the table below. All ingredient amounts are listed as kilogram per 1000 kilogram batch of product, unless otherwise specified.

| Ingredient | Ex. 2 | Ex. 3 | Ex. 4 | Ex. 5 | Ex. 6 |
| --- | --- | --- | --- | --- | --- |
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| 2-fucosyl-lactose (2FL) | 0.0948 | 0.090 | 0.085 | 9.479 | 9.005 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |

-continued

| Ingredient | Ex. 2 | Ex. 3 | Ex. 4 | Ex. 5 | Ex. 6 |
|---|---|---|---|---|---|
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.4 g | 47.4 g | 47.4 g | 47.4 g | 47.4 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

Examples 7-11

Examples 7-11 illustrate ready-to-feed nutritional emulsions for use in the methods of the present disclosure, the ingredients of which are listed in the table below. All ingredient amounts are listed as kilogram per 1000 kilogram batch of product, unless otherwise specified.

| Ingredient | Ex. 7 | Ex. 8 | Ex. 9 | Ex. 10 | Ex. 11 |
|---|---|---|---|---|---|
| Water | Q.S. | Q.S. | Q.S. | Q.S. | Q.S. |
| Condensed Skim Milk | 86.64 | 86.64 | 86.64 | 86.64 | 86.64 |
| Lactose | 54.80 | 54.80 | 54.80 | 54.80 | 54.80 |
| High oleic safflower oil | 14.10 | 14.10 | 14.10 | 14.10 | 14.10 |
| Soybean oil | 10.6 | 10.6 | 10.6 | 10.6 | 10.6 |
| Coconut oil | 10.1 | 10.1 | 10.1 | 10.1 | 10.1 |
| HMO Mixture | 0.0948 | 0.0901 | 0.0853 | 9.479 | 9.0047 |
| 6-sialyl-lactose (6SL) | 0.0316 | 0.0300 | 0.0284 | 0 | 0 |
| 2-fucosyl-lactose (2FL) | 0.0316 | 0.0300 | 0.0284 | 3.159 | 3.002 |
| Lacto-N-neotetraose (LNnT) | 0.0316 | 0.0300 | 0.0284 | 0 | 0 |
| Galactooligosaccharides (GOS) | 8.63 | 8.63 | 8.63 | 8.63 | 8.63 |
| Whey protein concentrate | 6.40 | 6.40 | 6.40 | 6.40 | 6.40 |
| Potassium citrate | 478.9 g | 478.9 g | 478.9 g | 478.9 g | 478.9 g |
| Calcium carbonate | 448.28 g | 448.28 g | 448.28 g | 448.28 g | 448.28 g |
| Soy lecithin | 355.74 g | 355.74 g | 355.74 g | 355.74 g | 355.74 g |
| Stabilizer | 355.74 g | 355.74 g | 355.74 g | 355.74 g | 355.74 g |
| ARA oil | 368.01 g | 368.01 g | 368.01 g | 368.01 g | 368.01 g |
| Nucleotide/chloride premix | 293.26 g | 293.26 g | 293.26 g | 293.26 g | 293.26 g |
| Potassium chloride | 226.45 g | 226.45 g | 226.45 g | 226.45 g | 226.45 g |
| Ascorbic acid | 445.94 g | 445.94 g | 445.94 g | 445.94 g | 445.94 g |
| Vitamin mineral premix | 142.88 g | 142.88 g | 142.88 g | 142.88 g | 142.88 g |
| DHA oil | 137.8 g | 137.8 g | 137.8 g | 137.8 g | 137.8 g |
| Carrageenan | 180.0 g | 180.0 g | 180.0 g | 180.0 g | 180.0 g |
| Magnesium chloride | 55.0 g | 55.0 g | 55.0 g | 55.0 g | 55.0 g |
| Ferrous sulfate | 58.0 g | 58.0 g | 58.0 g | 58.0 g | 58.0 g |
| Choline chloride | 53.9 g | 53.9 g | 53.9 g | 53.9 g | 53.9 g |
| Vitamin A, $D_3$, E, $K_1$ premix | 47.40 g | 47.40 g | 47.40 g | 47.40 g | 47.40 g |
| Citric acid | 29.77 g | 29.77 g | 29.77 g | 29.77 g | 29.77 g |
| Mixed carotenoid premix | 26.40 g | 26.40 g | 26.40 g | 26.40 g | 26.40 g |
| Sodium chloride | AN | AN | AN | AN | AN |
| L-carnitine | 3.31 g | 3.31 g | 3.31 g | 3.31 g | 3.31 g |
| Tricalcium phosphate | 15.65 g | 15.65 g | 15.65 g | 15.65 g | 15.65 g |
| Potassium phosphate monobasic | 13.67 g | 13.67 g | 13.67 g | 13.67 g | 13.67 g |
| Riboflavin | 2.42 g | 2.42 g | 2.42 g | 2.42 g | 2.42 g |
| Potassium hydroxide | AN | AN | AN | AN | AN |

AN = as needed

What is claimed is:

1. A method of modulating hypothalamic pituitary adrenal response in an individual, the method comprising:
   identifying an individual in need of modulating hypothalamic pituitary adrenal response; and
   administering to the individual a nutritional composition comprising 2-fucosyl-lactose.

2. The method of claim 1, wherein the nutritional composition is a liquid comprising from 0.001 mg/mL to about 20 mg/mL of 2-fucosyl-lactose.

3. The method of claim 1, wherein the nutritional composition is a liquid comprising from 0.001 mg/mL to about 10 mg/mL of 2-fucosyl-lactose.

4. The method of claim 1, wherein the nutritional composition is a liquid comprising from 0.001 mg/mL to about 5 mg/mL of 2-fucosyl-lactose.

5. The method of claim 1, wherein the nutritional composition is a powder comprising from about 0.0005% to about 5% of 2-fucosyl-lactose by weight of the powder.

6. The method of claim 1, wherein the nutritional composition is a powder comprising from about 0.01% to about 1% of 2-fucosyl-lactose by weight of the powder.

7. The method of claim 1, wherein the nutritional composition further comprises at least one of a fat, protein, and carbohydrate.

8. The method of claim 1, wherein the nutritional composition is an infant formula.

9. The method of claim 1, wherein the nutritional composition is administered to the individual with an amount of 2-fucosyl-lactose effective to reduce serum corticosterone levels.

10. A method of reducing a hypothalamic pituitary adrenal response in an individual affected by stress, the method comprising:

identifying an individual affected by stress; and
administering to the individual a nutritional composition comprising 2-fucosyl-lactose.

11. The method of claim 10, wherein the nutritional composition is a liquid comprising from 0.001 mg/mL to about 20 mg/mL of 2-fucosyl-lactose.

12. The method of claim 10, wherein the nutritional composition is a liquid comprising from 0.001 mg/mL to about 10 mg/mL of 2-fucosyl-lactose.

13. The method of claim 10, wherein the nutritional composition is a liquid comprising from 0.001 mg/mL to about 5 mg/mL of 2-fucosyl-lactose.

14. The method of claim 10, wherein the nutritional composition is a powder comprising from about 0.0005% to about 5% of 2-fucosyl-lactose by weight of the powder.

15. The method of claim 10, wherein the nutritional composition is a powder comprising from about 0.01% to about 1% of 2-fucosyl-lactose by weight of the powder.

16. The method of claim 10, wherein the nutritional composition is administered to the individual with an amount of 2-fucosyl-lactose effective to reduce serum corticosterone levels.

* * * * *